US010398715B2

(12) United States Patent
Hernandez et al.

(10) Patent No.: US 10,398,715 B2
(45) Date of Patent: Sep. 3, 2019

(54) METHODS FOR INCREASING BRAIN FUNCTIONALITY USING 2-FUCOSYL-LACTOSE

(71) Applicant: ABBOTT LABORATORIES, Abbott Park, IL (US)

(72) Inventors: Enrique Vazquez Hernandez, Ogijares (ES); Ricardo Rueda Cabrera, Granada (ES); Rachael Buck, Gahanna, OH (US); Maria Ramirez Gonzalez, Granada (ES); Alejandro Barranco Perez, Las Gabias (ES)

(73) Assignee: ABBOTT LABORATORIES, Abbott Park, IL (US)

( * ) Notice: Subject to any disclaimer, the term of this patent is extended or adjusted under 35 U.S.C. 154(b) by 129 days.

(21) Appl. No.: 14/428,247

(22) PCT Filed: Sep. 12, 2013

(86) PCT No.: PCT/US2013/059488
§ 371 (c)(1),
(2) Date: Mar. 13, 2015

(87) PCT Pub. No.: WO2014/043368
PCT Pub. Date: Mar. 20, 2014

(65) Prior Publication Data
US 2015/0231159 A1 Aug. 20, 2015

(30) Foreign Application Priority Data
Sep. 14, 2012 (EP) .................................. 12382356

(51) Int. Cl.
*A61K 31/702* (2006.01)
*A61K 31/7016* (2006.01)
*A23L 33/00* (2016.01)
*A23L 33/10* (2016.01)
*A23L 1/29* (2006.01)

(52) U.S. Cl.
CPC ............ *A61K 31/702* (2013.01); *A23L 1/296* (2013.01); *A23L 33/10* (2016.08); *A23L 33/40* (2016.08); *A23V 2002/00* (2013.01)

(58) Field of Classification Search
None
See application file for complete search history.

(56) References Cited

U.S. PATENT DOCUMENTS 5,891,698 A * 4/1999 Prieto ................ A01K 67/0278
435/100
2008/0021096 A1 1/2008 Maher
2011/2006649 8/2011 Bergonzelli et al.
2012/0172307 A1 7/2012 Davis et al.
2012/0172319 A1 7/2012 Chow et al.
2012/0172327 A1* 7/2012 Buck .................... A23L 1/296
514/54
2015/0238508 A1 8/2015 Hernandez

FOREIGN PATENT DOCUMENTS

| CA | 2822222 | 7/2012 |
|---|---|---|
| WO | 1996/09299 | 3/1996 |
| WO | 2010/115934 | 10/2010 |
| WO | 2011/005681 | 1/2011 |
| WO | 2012/092155 | 7/2012 |
| WO | 2012/092156 | 7/2012 |
| WO | 2012/092160 | 7/2012 |
| WO | WO12/092160 | * 7/2012 |

OTHER PUBLICATIONS

International Search Report and Written Opinion for PCT/US2013/059436 dated Nov. 11, 2013.
International Preliminary Report on Patentability for PCT/US2013/059436 dated Mar. 17, 2015.
International Search Report and Written Opinion for PCT/US2013/059488 dated Oct. 25, 2013.
International Preliminary Report on Patentability for PCT/US2013/059488 dated Mar. 17, 2015.
Communication in EP Application No. 12382354.4 dated Apr. 21, 2015.
Kunz, et al., "Lactose-Derived Oligosaccharides in the Milk of Elephants: Comparison with Human Milk," British Journal of Nutrition, vol. 82(5), pp. 391-399 (Nov. 1, 1999).
Kunz, et al., "Oligosaccharides in Human Milk: Structural, Functional, and Metabolic Aspects," Annual Review of Nutrition, vol. 20 (Jan. 2000), pp. 699-722.
Wang, Bing et al., "Dietary sialic acid supplementation improves learning and memory in piglets," Am. J. Clin. Nutr., vol. 85(2), pp. 561-569 (Jan. 2007).
Office Action in U.S. Appl. No. 14/428,260 dated Nov. 3, 2016.
Office Action in CA Application No. 2,884,487 dated Jun. 3, 2016.
First Office Action for CN Application No. 201380059274.1 dated Jan. 28, 2016.
Second Office Action for CN Application No. 201380059274.1 dated Nov. 17, 2016.
Matthies et al., "Fucose and fucosyllactose enhance in-vitro hippocampal long-term potentiation," Brain Research, vol. 725, No. 2, pp. 276-280, Jul. 1, 1996.
Office Action in U.S. Appl. No. 14/428,260 dated Jun. 16, 2017.
Exam Report from Malaysian Application No. PI 2015000645 dated Nov. 30, 2017.
Invitation to Respond to Written Opinion in SG Application No. 11201501976S dated Jan. 10, 2017.

* cited by examiner

Primary Examiner — Traviss C McIntosh, III
(74) Attorney, Agent, or Firm — Calfee, Halter & Griswold LLP

(57) ABSTRACT

Disclosed are methods for enhancing learning and/or memory, enhancing memory acquisition, memory retention and recall by inducing a higher long-term potentiation in hippocampal neuronal synapsis in individuals. The methods include administration of 2-fucosyl-lactose to an individual.

18 Claims, 3 Drawing Sheets

METHODS FOR INCREASING BRAIN FUNCTIONALITY USING 2-FUCOSYL-LACTOSE

CROSS REFERENCE TO RELATED APPLICATIONS

This application is the U.S. national stage entry of PCT/US2013/059488 with an an international filing date of Sep. 12, 2013, which claims priority to and any other benefit of EP application 12382356.9, filed Sep. 14, 2012, and entitled "METHODS FOR INCREASING BRAIN FUNCTIONALITY USING 2-FUCOSYL-LACTOSE," the entire disclosures of which are incorporated by reference herein.

FIELD OF THE DISCLOSURE

The present disclosure relates to human milk oligosaccharides, and in particular, 2-fucosyl-lactose (2FL), for enhancing learning and/or memory, enhancing memory acquisition, memory retention and recall in individuals. In some embodiments, the 2FL may be used to induce a higher long term potentiation in hippocampal neuronal synapsis.

BACKGROUND OF THE DISCLOSURE

Long-term potentiation (LTP) is a long-lasting enhancement in signal transmission between two neurons that results from stimulating the neurons synchronously. LTP is one of several phenomena underlying synaptic plasticity, the ability of chemical synapses to change their strength. At a cellular level, LTP enhances synaptic transmission as it improves the ability of two neurons, one presynaptic and the other postsynaptic, to communicate with one another across a synapse. Thus, LTP is a persistent increase in synaptic strength following high-frequency stimulation of a chemical synapse.

As learning and memory, both memory acquisition and memory recall, are thought to be encoded by modification of synaptic strength, LTP is widely considered one of the major cellular mechanisms that underlies those functions. LTP may account for many types of learning, from the relatively simple classical conditioning present in all animals, to the more complex, higher-level cognition observed in humans.

The hippocampus is a major component of the brain of humans, belonging to the limbic system. The hippocampus plays significant roles in the consolidation of information from short-term memory to long-term memory and spatial navigation. As different neuronal cell types are neatly organized into layers in the hippocampus, it has frequently been used as the model system for studying neurophysiology, and in particular, for studying LTP.

Various diseases and conditions affect hippocampus and its related functions, such as cognition, including both learning and memory. For example, stress, and stress-related hormones released in response to stress, affect the hippocampus in at least three ways: first, by reducing the excitability of some hippocampal neurons; second, by inhibiting the genesis of new neurons in the dentate gyrus; and third, by causing atrophy of dendrites in pyramidal cells of the CA3 region. There has now been evidence that humans that experience stress can affect hippocampal function, including learning and memory that may persist throughout life.

Accordingly, it would be desirable to provide nutritional compositions that provide individual components that can induce higher long-term potentiation in hippocampal neuronal synapsis, thereby enhancing cognitive performance, and particularly, memory acquisition, memory retention, and memory recall that may contribute to the learning and memory processes. It would also be beneficial if the nutritional compositions could be utilized early in life to maximize benefits throughout life.

SUMMARY OF THE DISCLOSURE

The present disclosure is directed to methods of improving brain functionality in an individual, including infants, pediatrics, adults, and older adults, using human milk oligosaccharides (HMOs), and in particular, 2-fucosyl-lactose alone or in combination with other HMOs. Particularly, the methods of the present disclosure include administering a nutritional composition including 2-fucosyl-lactose to an individual to induce higher long-term potentiation in hippocampal neuronal synapsis, thereby enhancing learning and memory, including memory acquisition, memory retention, and memory recall in the individual. The nutritional compositions and methods described herein may be particularly beneficial for infants, in some embodiments.

In one embodiment, the present disclosure is directed to a method of enhancing learning in an individual. The method comprises administering to the individual a nutritional composition comprising 2-fucosyl-lactose.

In another embodiment, the present disclosure is directed to a method of enhancing memory acquisition and memory recall in an individual. The method comprises administering to the individual a nutritional composition comprising 2-fucosyl-lactose.

In another embodiment the present disclosure is directed to a method of increasing brain functionality in an individual. The method comprises administering to the individual a nutritional composition comprising 2-fucosyl-lactose.

In another embodiment the present disclosure is directed to a method of inducing a higher long-term potentiation in the hippocampal neuronal synapsis in an individual. The method comprises administering to the individual a nutritional composition comprising 2-fucosyl-lactose.

In another embodiment the present disclosure is directed to a method of inducing a higher long-term potentiation of field excitatory post-synaptic potentials evoked at the hippocampal CA3-CA1 synapse in an individual. The method comprises administering to the individual a nutritional composition comprising 2-fucosyl-lactose.

In another embodiment, the present disclosure is directed to a method of improving neuronal development in the infant. The method comprises administering to the infant a nutritional composition comprising 2 fucosyl-lactose.

It has been unexpectedly discovered that human milk oligosaccharides, and particularly, 2-fucosyl-lactose, alone or in combination with one or more other HMOs, can enhance the hippocampal LTP response in an individual, including an infant. Particularly, administration of 2-fucosyl-lactose provides a larger, longer-lasting potentiation of field excitatory post-synaptic potential at the hippocampal CA3-CA1 synapse. Additionally, by inducing a higher long-term potentiation in hippocampal neuronal synapsis, an individual can experience enhanced learning and memory, including memory acquisition, retention, and recall.

DETAILED DESCRIPTION OF THE DISCLOSURE

Figure 1:
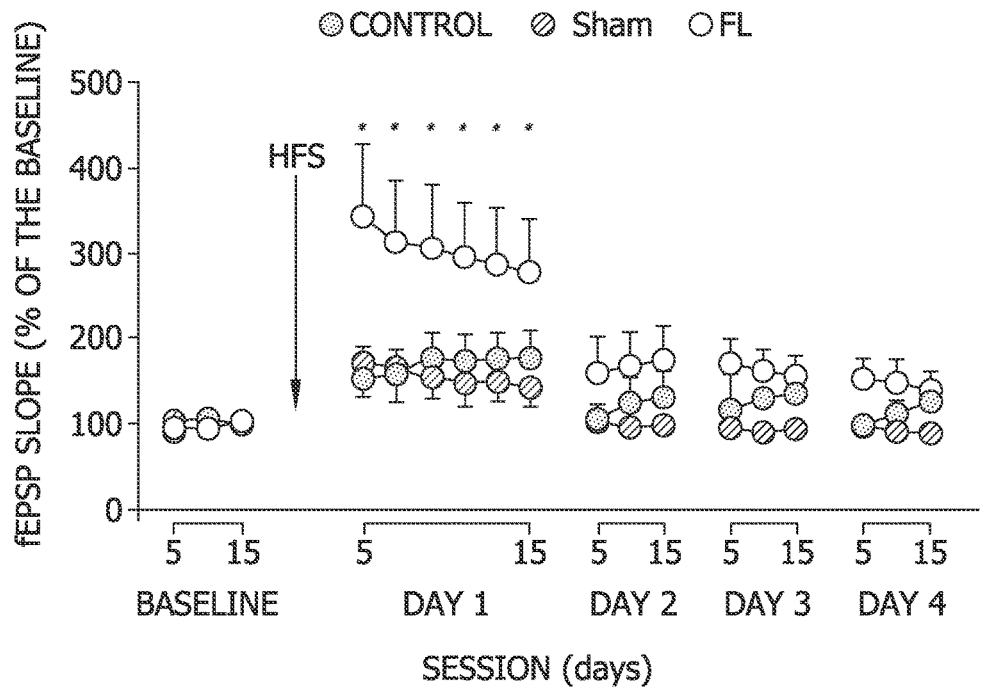
FIG. 1 is a graph depicting monosynaptic field excitatory post-synaptic potential (fEPSP) recordings as analyzed in Example 1.

The present disclosure is directed to methods for inducing a higher long-term potentiation in hippocampal neuronal synapsis, increasing brain functionality. The present methods generally include administering a nutritional composition including 2-fucosyl-lactose to an individual to enhance learning and memory. The methods may be useful in maintaining a healthy central nervous system, as well as have implications in providing improved cognitive functioning and/or performance to an individual. The compositions and methods described herein may provide an easy and effective means for increasing the brain functionality of an individual, including an infant.

These and other features of the compositions and methods, as well as some of the many optional variations and additions, are described in detail hereafter.

The terms "acute psychological stress" and "acute stress" as used herein, unless otherwise specified, are used interchangeably to refer to a psychological condition (e.g., feeling of strain, pressure, anxiety, being overwhelmed, irritability, nervousness, insecurity, depression, panic, exhaustion) arising in response to a terrifying or traumatic event. A "terrifying event" or "traumatic event" is an experience that causes the individual to experience disturbing or unexpected fear, stress or pain.

The terms "early stress" or "stress early in life" as used herein, unless otherwise specified, are used interchangeably to refer to the experience of stress early in an individual's life; that is, during the period ranging from birth to early adolescence. "Early adolescence" refers to the period of from 10 years to 14 years of life.

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", as used herein, unless otherwise specified, refers generally to a number of complex carbohydrates found in human breast milk that can be in acidic or neutral form, and to precursors thereof. Exemplary non-limiting human milk oligosaccharides include 2-fucosyl-lactose, 3-fucosyl-lactose, 3-sialyl-lactose, 6-sialyl-lactose, and lacto-N-neo-tetraose. Exemplary human milk oligosaccharide precursors include sialic acid and/or fucose.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which comprise one or more of fat, protein and carbohydrate and are suitable for oral consumption by a human.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The terms "susceptible" and "at risk" as used herein, unless otherwise specified, mean having little resistance to a certain condition or disease, including being genetically predisposed, having a family history of, and/or having symptoms of the condition or disease.

The terms "modulating" or "modulation" or "modulate" as used herein, unless otherwise specified, refer to the targeted movement of a selected characteristic.

The term "cognitive performance" as used herein, unless otherwise specified, refers to the learning, thinking, and memory functions (i.e., memory acquisition, memory retention and recall) of the brain. Accordingly, the term "improving cognitive performance" as used herein, unless otherwise specified, refers to improving the learning, thinking, and/or memory (memory acquisition, memory retention, and memory recall) functions of an individual.

The term "improving a cognitive impairment and/or brain dysfunction" as used herein, unless otherwise specified, refers to the treating, preventing, and/or reducing the incidence or severity of cognitive decline associated with age-related cognitive decline or neurodegenerative disease.

The term "age-related cognitive decline" as used herein, unless otherwise specified, refers to a gradual decline in learning, thinking, and/or memory functions that are normal consequences of aging.

The term "neurodegenerative disease" as used herein, unless otherwise specified, refers to the progressive loss of structure or function of neurons, including the death of neurons and includes diseases such as Parkinson's disease, Alzheimer's disease, Huntington's disease, dementia, amyotrophic lateral sclerosis, stroke, and schizophrenia.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the compositions used in the methods of the present disclosure may also be substantially free of any optional or selected ingredient or feature described herein, provided that the remaining composition still contains all of the required ingredients or features as described herein. In this context, and unless otherwise specified, the term "substantially free" means that the selected nutritional composition contains less than a functional amount of the optional ingredient, typically less than 1%, including less than 0.5%, including less than 0.1%, and also including zero percent, by weight of such optional or selected ingredient.

The compositions and methods may comprise, consist of, or consist essentially of the essential elements of the compositions and methods as described herein, as well as any additional or optional element described herein or otherwise useful in nutritional product applications.

Product Form

The nutritional compositions used in the methods of the present disclosure include a fucosylated human milk oligosaccharide, particularly 2-fucosyl-lactose (2FL), and may be formulated and administered in any known or otherwise suitable oral product form. Any solid, liquid, semi-solid, semi-liquid, or powder product form, including combinations or variations thereof, are suitable for use herein, provided that such forms allow for safe and effective oral delivery to the individual of the ingredients as also defined herein.

The compositions used in the methods of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof.

The nutritional compositions may be formulated with sufficient kinds and amounts of nutrients to provide a sole, primary, or supplemental source of nutrition, or to provide a specialized nutritional product for use in individuals afflicted with specific conditions or with a targeted nutritional benefit as described below.

Some exemplary, non-limiting, examples of specific products that may be suitable for use in accordance with the present disclosure include preterm infant formulas, term infant formulas, human milk fortifiers, pediatric formulas, adult nutritional formulas, older adult nutritional formulas, medical formulas, geriatric nutritional formulas, diabetic nutritional formulas, and the like.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to 95% by weight of water, including from about 50% to 95%, also including from about 60% to about 90%, and also including from about 70% to about 85%, of water by weight of the nutritional emulsions. The nutritional emulsions may have a variety of product densities, but most typically have a density greater than 1.03 g/mL, including greater than 1.04 g/mL, including greater than 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least 1 mL, or even at least 2 mL, or even at least 5 mL, or even at least 10 mL, or even at least 25 mL, including ranges from 1 mL to about 300 mL, including from about 4 mL to about 250 mL, and including from about 10 mL to about 240 mL.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

Methods of Inducing Higher Long-Term Potentiation (LTP)

The methods of the present disclosure use fucosylated human milk oligosaccharides-containing nutritional compositions, and in particular, 2-fucosyl-lactose (2FL)-containing nutritional compositions, to induce a higher long-term potentiation (LTP) in hippocampal neuronal synapsis in an individual. As noted, enhanced LTP increases brain functionality in an individual, and particularly, improves cognitive performance. Particularly, the administration of 2FL may improve general cognition by producing a sequential action on memory acquisition, memory retention and memory recall that contributes to the cognitive functions of learning, thinking, and memory.

Additionally, in some embodiments, the nutritional compositions can be utilized to improve a cognitive impairment and/or brain dysfunction that may be associated with age-related cognitive decline or cognitive decline associated with a neurodegenerative disease. Particularly, age-related conditions such as Alzheimer's disease, have a severe impact on many types of cognition, but even normal, healthy aging is associated with a gradual decline in some types of memory, including episodic memory and working memory. Because the hippocampus is thought to play a central role in memory, there has been considerable interest in the possibility that age-related declines could be caused by hippocampal deterioration. Specifically, there has been reported a reliable relationship between the size of the hippocampus and memory performance—meaning that not all elderly people show hippocampal shrinkage, but those who do tend to perform less well on some memory tasks. There are also reports that memory tasks tend to produce less hippocampal activation in elderly than in young subjects. Further, in rats, where detailed studies of cellular physiology are possible, aging has been found to alter synaptic connectivity in several ways. Functional synapses are lost in the dentate gyrus and CA1 region, and NMDA receptor-mediated responses are reduced. These changes may account for deficits in induction and maintenance of long-term potentiation. There are also age-related declines in hippocampal expression of several genes associated with synaptic plasticity. Other related disorders affected by hippocampal function include Huntington's disease, Parkinson's disease, dementia, amyotrophic lateral sclerosis, stroke, and/or schizophrenia. Accordingly, by enhancing hippocampal activity, the methods of the present disclosure can be used to reduce/prevent/control/treat cognitive impairment and/or brain dysfunction associated with these diseases and conditions.

Although in some embodiments the methods of the present disclosure may be directed to individuals who have a neurodegenerative disease or condition, or a disease or condition related to a neurodegenerative disease or condition, the methods of the present disclosure as described herein are also intended in some embodiments to include the use of such methods in "at risk" individuals, including individuals unaffected by or not otherwise afflicted with neurodegenerative diseases or conditions such as those described above, for the purpose of preventing, minimizing, or delaying the development of such diseases or conditions over time. For such prevention purposes, the methods of the present disclosure preferably include continuous, daily administration of the compositions as described herein. Such preventive methods may be directed at adults or others, particularly older adults (age 50 or older), who are susceptible to developing neurodegenerative diseases due to hereditary considerations, environmental considerations, and the like.

Additionally, the methods of the present disclosure may be used to reduce/prevent/control/treat cognitive impairment and/or brain dysfunction associated with psychological stress. Particularly, as noted above, stress and stress-release of hormones (e.g., corticosterone, cortisol, etc.) affect the hippocampus by reducing the excitability of some hippocampal neurons, inhibiting the genesis of new neurons in the dentate gyrus, and by causing atrophy of dendrites in pyramidal cells of the CA3 region. Further, evidence exists that stress experienced shortly after birth (i.e., early stress), can affect hippocampal function in ways that persist throughout life.

2-fucosyl-lactose (2FL) may be administered to a subset of individuals in need of inducing higher LTP and/or enhancing learning and memory. Some individuals that are in specific need of higher LTP and/or enhanced learning and memory may include infants, pediatrics, teens, or adults who experience acute psychological stress or stressful events (infants, pediatrics, teens, or adults susceptible to or at elevated risk of experiencing acute psychological stress or stressful events), infants, pediatrics, teens, or adults who experienced acute psychological stress early in life, non-breastfed infants, chronically depressed infants, pediatrics, teens, or adults (infants, pediatrics, teens, or adults susceptible to or at elevated risk of chronic depression), infants, pediatrics, teens, or adults affected by post-traumatic stress syndrome (infants, pediatrics, teens, or adults susceptible to or at elevated risk of post-traumatic stress syndrome), infants, pediatrics, teens, or adults affected by neurodegenerative diseases or conditions such as Alzheimer's disease, Huntington's disease, Parkinson's disease, dementia, amyotrophic lateral sclerosis, stroke, and/or schizophrenia (infants, pediatrics, teens, or adults susceptible to or at elevated risk of neurodegenerative diseases or conditions), adults affected by age-related cognitive decline (adults susceptible to or at elevated risk of age-related cognitive decline), and the like. Preterm infants, infants, pediatrics, teens, adults, and older adults may be susceptible to or at elevated risk of the above diseases or conditions due to family history, age, environment, and/or lifestyle. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases or conditions.

The individual desirably consumes at least one serving of the composition daily, and in some embodiments, may consume two, three, or even more servings per day. Each serving is desirably administered as a single, undivided dose, although the serving may also be divided into two or more partial or divided servings to be taken at two or more times during the day. The methods of the present disclosure include continuous day after day administration, as well as periodic or limited administration, although continuous day after day administration is generally desirable. The methods of the present disclosure are preferably applied on a daily basis, wherein the daily administration is maintained continuously for at least 3 days, including at least 5 days, including at least 1 month, including at least 4 weeks, including at least 8 weeks, including at least 2 months, including at least 6 months, desirably for at least 18-24 months, desirably as a long term, continuous, daily, dietary supplement.

2-Fucosyl-Lactose (2FL)

The methods of the present disclosure for inducing enhanced hippocampal LTP utilize compositions that include 2-fucosyl-lactose (2FL). The 2FL used in the composition may be isolated or enriched from milk(s) secreted by mammals including, but not limited to: human, bovine, ovine, porcine, or caprine species. 2FL may also be produced via microbial fermentation, enzymatic processes, chemical synthesis, or combinations thereof.

2FL is present in the compositions in an amount (mg of 2FL per mL of composition) of at least 0.001 mg/mL, including at least 0.01 mg/mL, including from 0.001 mg/mL to about 20 mg/mL, including from about 0.01 mg/mL to about 20 mg/mL, including from 0.001 mg/mL to about 10 mg/mL, including from about 0.01 mg/mL to about 10 mg/mL, including from 0.001 mg/mL to about 5 mg/mL, including from about 0.01 mg/mL to about 5 mg/mL, including from 0.001 mg/mL to about 1 mg/mL, including from 0.001 mg/mL to about 0.23 mg/mL, including from about 0.01 mg/mL to about 0.23 mg/mL of 2FL in the composition. Typically, the amount of 2FL present in the composition will depend on the amounts of other components in the compositions, including the amounts any optional other human milk oligosaccharides as described below.

In one specific embodiment when the composition is a nutritional powder, the concentration of 2FL in the nutritional powder is from about 0.0005% to about 5%, including from about 0.01% to about 1% (by weight of the nutritional powder).

In another specific embodiment, when the product is a ready-to-feed nutritional liquid, the concentration of 2FL in the ready-to-feed nutritional liquid is from about 0.0001% to about 0.50%, including from about 0.001% to about 0.15%, including from about 0.01% to about 0.10%, and further including from about 0.01% to about 0.03% (by weight of the ready-to-feed nutritional liquid).

In another specific embodiment when the product is a concentrated nutritional liquid, the concentration of 2FL in the concentrated nutritional liquid is from about 0.0002% to about 0.60%, including from about 0.002% to about 0.30%, including from about 0.02% to about 0.20%, and further including from about 0.02% to about 0.06% (by weight of the concentrated nutritional liquid).

Optional Additional Sialylated or Fucosylated Human Milk Oligosaccharides

In addition to the 2FL described above, the compositions may optionally include additional sialylated or fucosylated human milk oligosaccharides. The additional human milk oligosaccharide(s) used in the composition may be isolated or enriched from milk(s) secreted by mammals including, but not limited to: human, bovine, ovine, porcine, or caprine species. The human milk oligosaccharides may also be produced via microbial fermentation, enzymatic processes, chemical synthesis, or combinations thereof.

Suitable sialylated human milk oligosaccharides for optional use in the compositions include at least one sialic acid residue in the oligosaccharide backbone. The sialylated human milk oligosaccharide may include two or more sialic acid residues also. Specific non-limiting examples of sialylated human milk oligosaccharides for use in the present disclosure include sialyl oligosaccharides, sialic acid (i.e., free sialic acid, lipid-bound sialic acid, protein-bound sialic acid), lactosialotetraose, 3'-Sialyl-3-fucosyllactose, Disialomonofucosyllacto-N-neohexaose, Monofucosylmonosialyl-lacto-N-octaose (sialyl Lea), Sialyllacto-N-fucohexaose II, Disialyllacto-N-fucopentaose II, Monofucosyldisialyllacto-N-tetraose), sialyl fucosyl oligosaccharides, 2'-Sialyllactose, 2-Sialyllactosamine, 3'-Sialyllactose, 3'-Sialyllactosamine, 6'-Sialyllactose, 6'-Sialyllactosamine, Sialyllacto-N-neotetraose c, Monosialyllacto-N-hexaose, Disialyllacto-N-hexaose I, Monosialyllacto-N-neohexaose I, Monosialyl-lacto-N-neohexaose II, Disialyllacto-N-neohexaose, Disialyllacto-N-tetraose, Disialyllacto-N-hexaose II, Sialyl-lacto-N-tetraose a, Disialyllacto-N-hexaose I, Sialyllacto-N-tetraose b, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, disialyl-lacto-N-tetraose and combinations thereof. Particularly desirable sialylated human milk oligosaccharides include 3'Sialyllactose, 6'Sialyllactose, and combinations thereof.

Specific non-limiting examples of additional optional fucosylated human milk oligosaccharides for use in the present disclosure include fucosyl oligosaccharides, Lacto-N-fucopentaose I, Lacto-N-fucopentaose II, 3'-Fucosyllactose, Lacto-N-fucopentaose III, Lacto-N-difucohexaose I, Lactodifucotetraose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaosemonofucosyl-lacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-fucopentaose V, lacto-N-decaose, trifucosyllacto-N-neooctaose, trifucosyllacto-N-octaose, trifucosyl-iso-lacto-N-octaose, lacto-N-difuco-hexaose II, and combinations thereof.

Other suitable examples of human milk oligosaccharides that may be included in the compositions for use in the methods of the present disclosure include lacto-N-hexaose, para-lacto-N-hexaose, lacto-N-neohexaose, para-lacto-N- neohexaose, lacto-N-neoocataose, para-lacto-N-octanose, iso-lacto-N-octaose, lacto-N-octaose, and combinations thereof.

The sialylated and fucosylated human milk oligosaccharides (inclusive of 2FL) may be present in the compositions in a total amount of human milk oligosaccharide in the composition (mg of human milk oligosaccharide per mL of composition) of at least 0.001 mg/mL, including at least 0.01 mg/mL, including from 0.001 mg/mL to about 20 mg/mL, including from about 0.01 mg/mL to about 20 mg/mL, including from 0.001 mg/mL to about 10 mg/mL, including from about 0.01 mg/mL to about 10 mg/mL, including from 0.001 mg/mL to about 5 mg/mL, including from about 0.01 mg/mL to about 5 mg/mL, including from 0.001 mg/mL to about 1 mg/mL, including from 0.001 mg/mL to about 0.23 mg/mL, including from about 0.01 mg/mL to about 0.23 mg/mL of total human milk oligosaccharide in the composition. Typically, the amount of specific sialylated human milk oligosaccharide and/or fucosylated human milk oligosaccharide (inclusive of 2FL) present in the composition will depend on the specific human milk oligosaccharide or human milk oligosaccharides present and the amounts of other components in the compositions, including the amounts of any optional human milk oligosaccharides.

Macronutrients

The compositions including 2FL may be formulated to include at least one of fat, protein, and carbohydrate. In many embodiments, the nutritional compositions will include 2FL with fat, protein, and carbohydrate.

Although total concentrations or amounts of the fat, protein, and carbohydrates may vary depending upon the product type (i.e., human milk fortifier, preterm infant formula, infant formula, pediatric formula, adult formula, medical formula, etc.), product form (i.e., nutritional solid, powder, ready-to-feed liquid, or concentrated liquid) and targeted dietary needs of the intended user, such concentrations or amounts most typically fall within one of the following embodied ranges, inclusive of any other essential fat, protein, and/or carbohydrate ingredients as described herein.

For infant and adult formulas, carbohydrate concentrations most typically range from about 5% to about 40%, including from about 7% to about 30%, including from about 10% to about 25%, by weight; fat concentrations most typically range from about 1% to about 30%, including from about 2% to about 15%, and also including from about 3% to about 10%, by weight; and protein concentrations most typically range from about 0.5% to about 30%, including from about 1% to about 15%, and also including from about 2% to about 10%, by weight.

The amount of fats, proteins, and/or carbohydrates in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total Cal. | Embodiment A | Embodiment B | Embodiment C | Embodiment D | Embodiment E | Embodiment F |
|---|---|---|---|---|---|---|
| Carbohydrate | 0-98 | 2-96 | 10-75 | 30-50 | 25-50 | 25-50 |
| Protein | 0-98 | 2-96 | 5-70 | 15-35 | 10-30 | 5-30 |
| Fat | 0-98 | 2-96 | 20-85 | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, including from about 20% to about 50% by weight of the human milk fortifier.

The total amount or concentration of fat, carbohydrate, and protein, in the powdered nutritional compositions used herein can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered product. For powdered nutritional compositions, such total amounts or concentrations are most typically and preferably formulated within any of the embodied ranges described in the following table (each numerical value is preceded by the term "about").

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional compositions used in the methods of the present disclosure may include a source or sources of fat. Suitable sources of fat for use herein include any fat or fat source that is suitable for use in an oral nutritional product and is compatible with the elements and features of such products. For example, in one specific embodiment, the fat is derived from long chain polyunsaturated fatty acids and/or short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions used in the methods of the present disclosure may optionally further comprise protein. Any protein source that is suitable for use in oral nutritional compositions and is compatible with the elements and features of such products is suitable for use in the nutritional compositions.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy, pea) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, intact pea protein concentrates, intact pea protein isolates, hydrolyzed pea protein concentrates, hydrolyzed pea protein isolates, and so forth. In one specific embodiment, the nutritional compositions include a protein source derived from milk proteins of human and/or bovine origin.

Carbohydrate

The nutritional products as used in the methods of the present disclosure may further optionally comprise any carbohydrates that are suitable for use in an oral nutritional product and are compatible with the elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions as used in the methods of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, and other prebiotics, probiotics, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from about 0.1% to about 10%, and also including from about 1% to about 6%, by weight of the nutritional product. Optional artificial sweetener concentrations may range from at least 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Methods of Manufacture

The nutritional compositions used in the methods of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions used in the methods of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., 2FL, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective technique, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference to the extent that they are consistent herewith.

EXAMPLES

The following examples illustrate specific embodiments and/or features of the nutritional compositions used in the methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

Example 1

In this Example, the effect of 2-fucosyl-lactose on hippocampal LTP response in early stressed maternally deprived mice was analyzed.

Initially, mice pups were early stressed using a model of maternal separation. Particularly, one day after delivery, C57BL/6 mice pups were sexed and grouped as sham (non-stressed Control group) or maternally separated (MS—stressed group) animals. From day 2 until day 14 after delivery, the MS pups were removed from the dam and kept isolated for a period of 4 hours per day, typically, from 10:00 AM to 2:00 PM, in a thermostatted cup. During the same time period, pups from the sham group were daily handled for a period of five minutes in order to receive the same grade of habituation to a researcher's hands as the MS pups.

Each dam had litters of 4 males and 2 females. Females were allowed to stay with the mother, while males were maternally deprived in order to avoid stressing the dam by removing all of the pups. Additionally, pups from the MS group were prematurely weaned, and thus permanently removed from the dam, at postnatal day 17, whereas sham pups were not weaned until postnatal day 21. At postnatal day 22, all pups in the MS group were pooled and two experimental groups were made before starting nutritional intervention. The three total groups are shown in the table below.

| Experimental Group | Experimental Conditions |
|---|---|
| Sham Control Group | Normal mice not MS-stressed receiving AIN-93G diet and water. |
| MS Control Group | MS-stressed mice receiving AIN-93G diet and water. |
| MS 2-fucosyllactose Group | MS-stressed mice receiving AIN93G diet supplemented with 2-fucosyllactose (~7 mg/day/mouse) and water. |

At the nutritional intervention stage, mice were fed experimental diets for a period of eight weeks. After eight weeks, the mice were anesthetized and implanted with stimulating and recording electrodes in the hippocampus. Specifically, stereotaxic coordinates were followed to implant animals with stimulating electrodes aimed at the Schaffer collateral-commissural pathway of the dorsal hippocampus (2 mm lateral and 1.5 mm posterior to Bregma; 1.0-1.5 mm depth from brain surface). In addition, the mice were implanted with recording electrodes aimed at the ipsilateral stratum radiatum underneath the CA1 area (1.2 mm lateral and 2.2 mm posterior to Bregma; 1.0-1.5 mm depth from brain surface). Electrodes were surgically implanted in the CA1 area using as a guide the field potential depth profile evoked by paired (20-50 ms of interval) pulses presented at the ipsilateral Schaffer collateral pathway. The recording electrodes were fixed at the site where a reliable monosynaptic field excitatory post-synaptic potential (fEPSP) was recorded. A 0.1 mm bare silver wire was affixed to the skull as a ground. The wires were connected to two four-pin sockets (available from RS-Amidata, Madrid, Spain). The ground wire was also connected to the recording system with a single wire. Sockets were fixed to the skull with the help of two small screws and dental cement.

Recordings were carried out using Grass P511 differential amplifiers with a bandwidth of 0.1 Hz-10 kHz (Grass-Telefactro, West Warwick, R.I.). Synaptic field potentials in the CA1 area were evoked by paired (40 ms of interval) 100 μs, square, biphasic (negative-positive) pulse applied to Schaffer collaterals. Stimulus intensities ranged from 50 to 350 μA. For each animal, the stimulus intensity was set well below the threshold for evoking a population spike, usually 30-40% of the intensity necessary for evoking a maximum fEPSP response. An additional criterion for selecting stimulus intensity was that a second stimulus, presented 20-50 ms after a conditioning pulse, evoked a larger (>20%) synaptic field potential.

For evoking LTP, each animal was presented with five 200 Hz, 100 μs trains of pulses at a rate of 1/s. These trains were presented six times in total, at intervals of one minute. The 100 μs, square, biphase pulses used to evoke LTP were applied at the same intensity used for evoking baseline records. Baseline records were collected for 15 minutes with the paired stimuli presented every 20 s. After, fEPSPs were recorded again for 30 minutes. Additional recordings were carried out for 15 minutes during the following three days. The results are shown in FIG. 1.

As shown in FIG. 1, the group fed 2FL exhibited a larger, longer-lasting potentiation of field excitatory post-synaptic potentials evoked at the hippocampal CA3-CA1 synapse when compared with the control groups (p<0.05).

Example 2

In this Example, the effect of 2FL on LTP of the hippocampal CA3-CA1 synapse in alert behaving rats was analyzed, Animals and Groups A total of four male Sprague Dawley rats, each 2 months old weighing from 150-200 g, were placed in individual cages with food and water ad libitum. Rats were kept on a 12/12 hour light/dark cycle with constant ambient temperature (22±1° C.) and humidity (50±7%). All tests were conducted during the light cycle.

Surgery and Electrode Implantation Procedures

The rats were anesthetized with 0.8%-3% isofluorane (available from AstraZeneca, Madrid, Spain) delivered via a home-made mask. Halothane was administered from a calibrated Fluotec 5 vaporizer (available from Fluotec-Ohmeda, Tewksbury, Mass.) at a flow rate of 1-4 L/min oxygen. Once anesthetized, the rats were implanted with stimulating and recording electrodes in the hippocampus. Specifically, stereotaxic coordinates were followed to implant the rats with three stimulating electrodes (made of 50 μm Teflon-coated tungsten wires available from Advent Research Materials Ltd., Eynsham, England) aimed at the right (contralateral) Schaffer collateral-commissural pathway of the dorsal hippocampus (3.5 mm lateral and 3.2 mm posterior to Bregma). In addition, the rats were implanted with four recording electrodes (made of 50 μm Teflon-coated tungsten wires available from Advent Research Materials Ltd., Eynsham, England) aimed at the ipsilateral stratum radiatum underneath the CA1 area (2.5 mm lateral and 3.6 mm posterior to Bregma). Electrodes were surgically implanted in the CA1 area using as a guide the field potential depth profile evoked by paired (20-50 ms of interval) pulses presented at the ipsilateral Schaffer collateral pathway. The recording electrodes were fixed at the site where a reliable monosynaptic field excitatory post-synaptic potential (fEPSP) was recorded. A 0.1 mm bare silver wire was affixed to the skull as a ground. The wires were connected to two sockets (available from RS-Amidata, Madrid, Spain). The ground wire was also connected to the recording system with a single wire. Sockets were fixed to the skull with the help of two small screws and dental cement.

Recordings were carried out using Grass P511 differential amplifiers with a bandwidth of 0.1 Hz-10 kHz (Grass-Telefactor, West Warwick, R.I.). Synaptic field potentials in the CA1 area were evoked by paired (40 ms of interval) 100 μs, square, biphasic (negative-positive) pulse applied to Schaffer collaterals. Stimulus intensities ranged from 50 to 350 μA. For each rat, the stimulus intensity was set well below the threshold for evoking a population spike, usually 30-40% of the intensity necessary for evoking a maximum fEPSP response. An additional criterion for selecting stimulus intensity was that a second stimulus, presented 20-50 ms after a conditioning pulse, evoked a larger (>20%) synaptic field potential.

Input/Output Curves and Paired-Pulse Test

Single pulses of increasing intensities (usually from 0.02 to 0.4 mA in steeps of 0.02 mA) were used for input/output curves. Each stimulus was repeated 5 times. Time interval between successive stimulus presentations was >20 seconds to avoid after effects of the preceding pair or stimulus.

A stimulus intensity (in mA) of about 35% of the total necessary to reach asymptotic values for the input/output study was selected for the paired-pulse test. The paired-pulse stimuli were presented at intervals of 10, 20, 40, 100, 200 and 500 ms. Each pair of stimuli was repeated five times. Time interval between successive stimulus presentations was >20 seconds to avoid after effects of the preceding pair of stimulus.

Control values for input/output curves and paired-pulse facilitation in the four rats were determined. The rats were then administered p.o. with 1 g/kg of 2FL dissolved in gelatin. Both input/output and paired-pulse tests were repeated 90 min and 180 min after the administration of the 2FL.

LTP Induction in Behaving Rats

For evoking LTP, each rat was presented with five 200 Hz, 100 ms trains of pulses at a rate of 1/s. These trains were presented 6 times in total, at intervals of one minute. The 100 µs, square, biphasic pulses used to evoke LTP were applied at the same intensity used for evoking baseline records. Baseline records were collected for 15 minutes with the paired stimuli presented every 20 seconds. After, fEPSPs were recorded again for 30 minutes. Additional recordings were carried out for 20 minutes the following day.

Results

Figure 2:
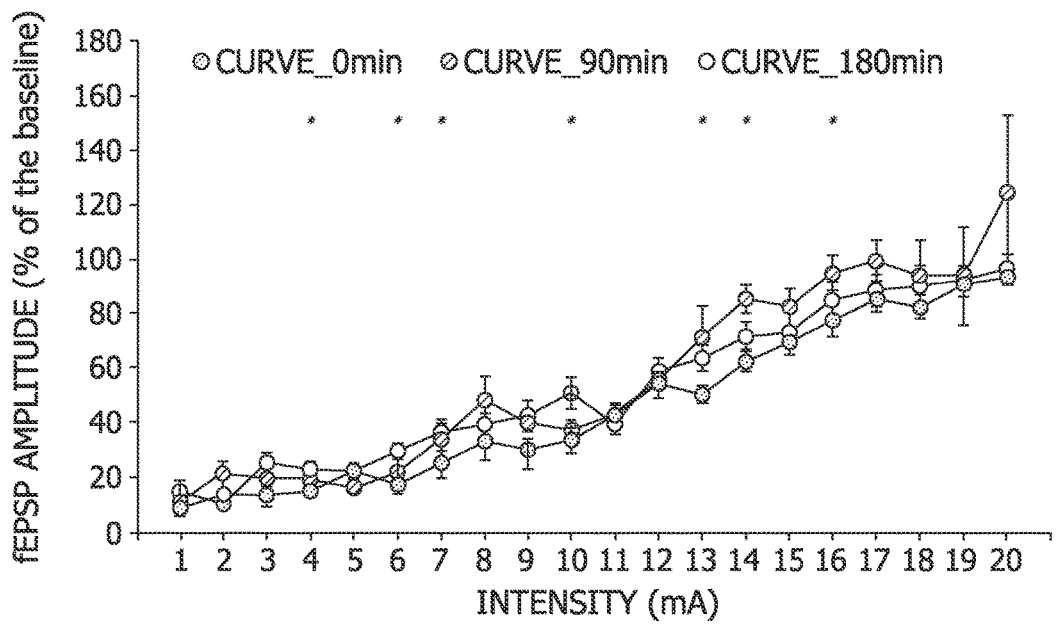
FIG. 2 is a graph depicting input/output curves evoked at the hippocampal CA3-CA1 synapse before and after the administration of 2FL to alert behaving rats as analyzed in Example 2.

As shown in FIG. 2, the use of single pulses of increasing intensities evoked fEPSP of increasing amplitude. Specifically, the amplitude of fEPSPs evoked at the CA3-CA1 synapse was significantly larger 90 and 180 minutes after 2FL administration.

Figure 3:
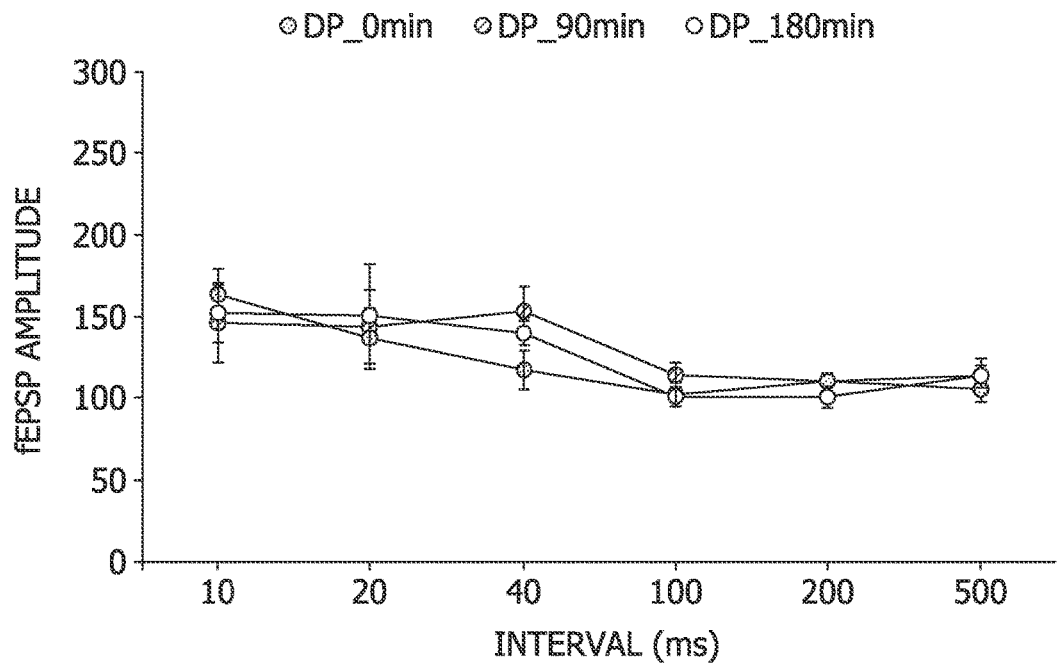
FIG. 3 is a graph depicting paired-pulse stimulation before and after administration of 2FL to alert behaving rats as analyzed in Example 2.

As shown in FIG. 3, the paired-pulse test indicated a significant ($P<0.05$) facilitation to the second pulse at short (10, 20, 40 ms), but not as long (>100 ms) intervals. Although facilitation values evoked at 40 ms of inter-pulse intervals were lower before than after 2FL administration, no significant differences were found between the three recording sessions.

Figure 4:
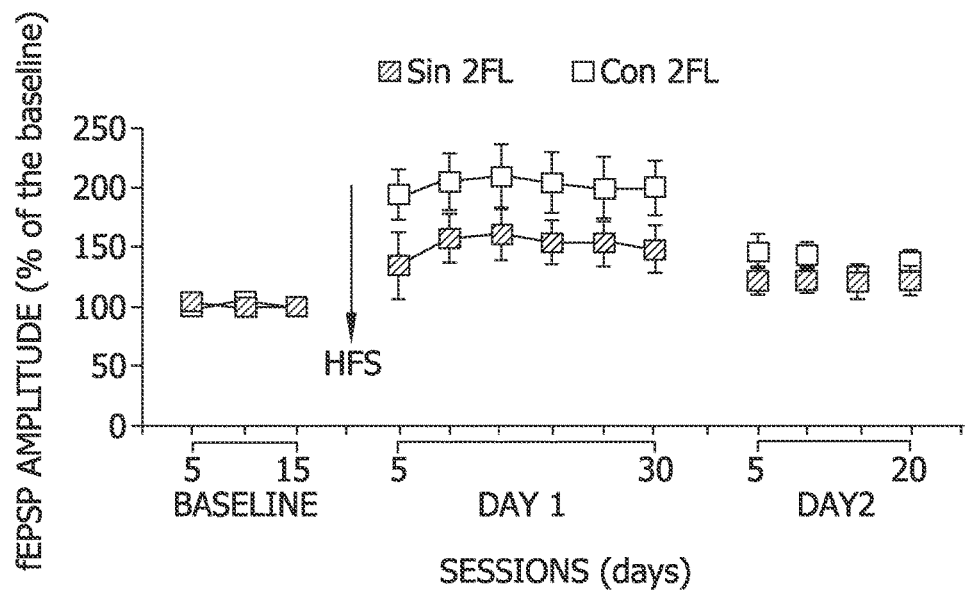
FIG. 4 is a graph depicting experimentally evoked LTP before and after administration of 2FL to alert behaving rats as analyzed in Example 2.

The two recording sessions carried out following HFS of the hippocampal CA3-CA1 synapse evoked a significant LTP (see FIG. 4). Further, the LTP evoked after 15 days of daily administration of 1 g/kg of 2FL presented significantly larger fEPSPs than control values.

Based on these results, it appears that the administration of 2FL has a facilitatory effect on input-output curves, and mainly on LTP evoked at the hippocampal CA3-CA1 synapse.

Example 3

In this Example, the effect of 2FL on Acetylcholinesterase (AChE) in zebrafish embryos was analyzed.

Zebrafish embryos were grown in water for 96 post-fertilization hours, when eclosion occurs. The larvae were then transferred into a 24-well culture dish and incubated for 24 hours at 26° C. in a dilution of 74.73 mg of 2FL per liter. A negative control (water) and a positive control for AChE (100 mg docosahexaenoic acid/liter) were included in the assay.

After incubation, larvae were homogenized and centrifuged. AChE levels and total protein content were determined in the resultant supernatants. Two separate assays were done in triplicates. Specific AChE activity data were referred to control and analyzed by ANOVA. Bonferroni post hoc tests were used for comparisons.

Figure 5:
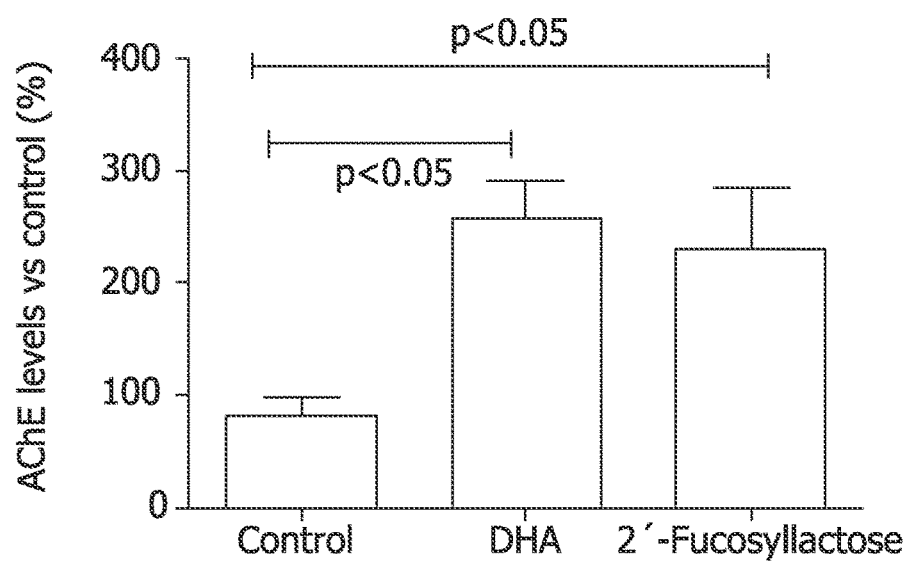
FIG. 5 is a graph depicting AChE levels after administration DHA and 2FL as compared to a control as analyzed in Example 3.

As shown in FIG. 5, 2FL induced a significant increase on the AChE levels when compared to the negative control and had a similar response to the positive control.

Examples 4-8

Examples 4-8 illustrate ready-to-feed nutritional emulsions for use in the methods of the present disclosure, the ingredients of which are listed in the table below. All ingredient amounts are listed as kilogram per 1000 kilogram batch of product, unless otherwise specified.

| Ingredient | Ex. 4 | Ex. 5 | Ex. 6 | Ex. 7 | Ex. 8 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2-fucosyl-lactose (2FL) | 0.0948 | 0.090 | 0.085 | 9.479 | 9.005 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.4 g | 47.4 g | 47.4 g | 47.4 g | 47.4 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 9-13

Examples 9-13 illustrate ready-to-feed nutritional emulsions for use in the methods of the present disclosure, the ingredients of which are listed in the table below. All ingredient amounts are listed as kilogram per 1000 kilogram batch of product, unless otherwise specified.

| Ingredient | Ex. 9 | Ex. 10 | Ex. 11 | Ex. 12 | Ex. 13 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| HMO Mixture | 0.0948 | 0.0901 | 0.0853 | 9.479 | 9.0047 |
| 6-sialyl-lactose (6SL) | 0.0316 | 0.0300 | 0.0284 | 0 | 0 |
| 2-fucosyl-lactose (2FL) | 0.0316 | 0.0300 | 0.0284 | 3.159 | 3.002 |
| Lacto-N-neotetraose (LNnT) | 0.0316 | 0.0300 | 0.0284 | 0 | 0 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

What is claimed is:

1. A method for the treatment of at least one of cognitive impairment and brain dysfunction in an individual, wherein the cognitive impairment and/or brain dysfunction are associated with psychological stress, the method comprising administering a nutritional composition comprising 2-fucosyl-lactose to an individual in need thereof, wherein the treatment results in enhanced learning in the individual.

2. The method of claim 1 wherein the nutritional composition is a liquid and comprises from 0.001 mg/mL to about 20 mg/mL of 2-fucosyl-lactose.

3. The method of claim 1 wherein the nutritional composition is a liquid and comprises from 0.001 mg/mL to about 10 mg/mL of 2-fucosyl-lactose.

4. The method of claim 1 wherein the nutritional composition is a liquid and comprises from 0.001 mg/mL to about 5 mg/mL of 2-fucosyl-lactose.

5. The method of claim 1 wherein the nutritional composition is a powder and comprises from about 0.0005% to about 5% of 2-fucosyl-lactose by weight of the powder.

6. The method of claim 1 wherein the nutritional composition is a powder and comprises from about 0.01% to about 1% of 2-fucosyl-lactose by weight of the powder.

7. The method of claim 1 wherein the nutritional composition further comprises at least one of a fat, protein, and carbohydrate.

8. The method of claim 1 wherein the nutritional composition is an infant formula.

9. The method of claim 1 wherein the individual is selected from: infants, pediatrics, teens, or adults who experience acute psychological stress or stressful events; non-breastfed infants; chronically depressed infants pediatrics, teens, or adults; those susceptible to or at elevated risk of post-traumatic stress syndrome; those affected by neurodegenerative diseases or conditions such as Alzheimer's disease, Huntington's disease, Parkinson's disease, dementia, amyotrophic lateral sclerosis, stroke, or schizophrenia; and combinations thereof.

10. A method for the treatment of at least one of: cognitive impairment and brain dysfunction in an individual, wherein the cognitive impairment and/or brain dysfunction are associated with psychological stress, the method comprising administering a nutritional composition comprising 2-fucosyl-lactose to an individual in need thereof, wherein the treatment results in enhanced memory acquisition and memory recall in the individual.

11. The method of claim 10 wherein the nutritional composition is a liquid and comprises from 0.001 mg/mL to about 20 mg/mL of 2-fucosyl-lactose.

12. The method of claim 10 wherein the nutritional composition is a liquid and comprises from 0.001 mg/mL to about 10 mg/mL of 2-fucosyl-lactose.

13. The method of claim 10 wherein the nutritional composition is a liquid and comprises from 0.001 mg/mL to about 5 mg/mL of 2-fucosyl-lactose.

14. The method of claim 10 wherein the nutritional composition is a powder and comprises from about 0.0005% to about 5% of 2-fucosyl-lactose by weight of the powder.

15. The method of claim 10 wherein the nutritional composition is a powder and comprises from about 0.01% to about 1% of 2-fucosyl-lactose by weight of the powder.

16. The method of claim 10 wherein the individual is selected from: infants, pediatrics, teens, or adults who experience acute psychological stress or stressful events; non-breastfed infants; chronically depressed infants pediatrics, teens, or adults; those susceptible to or at elevated risk of post-traumatic stress syndrome; those affected by neurodegenerative diseases or conditions such as Alzheimer's disease, Huntington's disease, Parkinson's disease, dementia, amyotrophic lateral sclerosis, stroke, or schizophrenia; and combinations thereof.

17. A method of treating at least one of: cognitive impairment and brain dysfunction in an individual, wherein the cognitive impairment and/or brain dysfunction are associated with acute psychological stress, the method comprising administering a nutritional composition comprising 2-fucosyl-lactose to an individual in need thereof.

18. The method of claim 17 wherein the individual is selected from: infants, pediatrics, teens, or adults who experience acute psychological stress or stressful events; non-breastfed infants; chronically depressed infants pediatrics, teens, or adults; those susceptible to or at elevated risk of post-traumatic stress syndrome; those affected by neurodegenerative diseases or conditions such as Alzheimer's disease, Huntington's disease, Parkinson's disease, dementia, amyotrophic lateral sclerosis, stroke, or schizophrenia; and combinations thereof.

* * * * *